United States Patent [19]

Forte et al.

[11] 4,172,452
[45] Oct. 30, 1979

[54] FRACTURE NAIL PLATE ASSEMBLY

[75] Inventors: Mark R. Forte, Pinebrook; Theodore J. Helder, Fairlawn, both of N.J.

[73] Assignee: Howmedica, Inc., New York, N.Y.

[21] Appl. No.: 905,805

[22] Filed: May 15, 1978

[51] Int. Cl.² .......................... A61F 5/04; A61B 17/18
[52] U.S. Cl. .............................. 128/92 BA; 128/92 D
[58] Field of Search ........... 128/92 BA, 92 BB, 92 D, 128/92 R, 92 B

[56] References Cited

U.S. PATENT DOCUMENTS

| 1,105,105 | 7/1914 | Sherman | 128/92 D |
| 2,937,642 | 5/1960 | Lange et al. | 128/92 BA |
| 3,107,666 | 10/1963 | Cecere et al. | 128/92 BA |
| 3,561,437 | 2/1971 | Orlich | 128/92 BA |
| 4,009,712 | 3/1977 | Burstein et al. | 128/92 BA |

FOREIGN PATENT DOCUMENTS 451868 10/1948 Canada .................................. 128/92 D Primary Examiner—Ronald L. Frinks
Attorney, Agent, or Firm—Connolly and Hutz

[57] ABSTRACT

A hip fracture nail device includes a telescopic nail for fixing the broken hip joint portions of the femur together and a retaining plate to which the nail is angularly secured in longitudinal sliding relationship at an angle of approximately 150° by a slanted bushing. The retaining plate has strong triangular prongs which engage within corresponding grooves in the sides of the bushing, which facilitate retention, removal, and sliding adjustment between them. The retaining plate is affixed to the shaft of the femur by a row of bone screws. The nail is manipulated by a tool connected to the inner end of the nail inserted through an aperture in the retaining plate. The nail is maintained at an adjusted distance from the bushing and plate by frictional engagement of a C-shaped retaining spring disposed between the outer wall of the nail and the inner wall of the bushing. Insertion and assembly of the C-shaped spring is accomplished through a pair of longitudinal slots in the outer wall of the nail disposed 180° relative to each other and a pin in the outer end of the bushing which passes between the free ends of the C-shaped spring.

3 Claims, 12 Drawing Figures

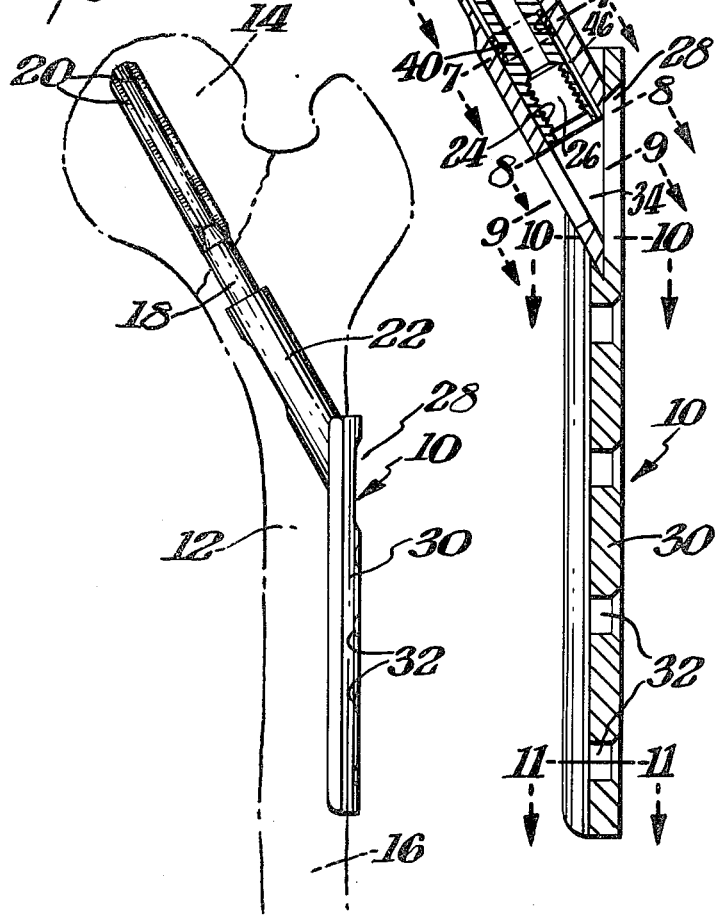

FRACTURE NAIL PLATE ASSEMBLY

BACKGROUND OF THE INVENTION

A fracture nail for fixing the broken ends of the hip joint portions of a femur and its method of implantation and use are described in U.S. Pat No. 2,937,642. Such a nail should be relatively strong without requiring excessive space and should be relatively easy to assemble, disassemble, adjust and readjust during implantation and removal. An object of this invention is to provide such a nail and retaining plate assembly, which is relatively strong and capable of ready assembly, disassembly, adjustment and readjustment during implantation and removal.

SUMMARY OF THE INVENTION

In accordance with this invention a hip fracture nail device includes a telescopic nail for fixing the broken hip joint portions of the femur together and a retaining plate to which the nail is secured in longitudinal sliding relationship at an angle of approximately 150° by a slanted bushing. The retaining plate has strong triangular prongs which engage within corresponding grooves in the sides of the bushing, which facilitate retention, removal, and sliding adjustment between them. The retaining plate is affixed to the shaft of the femur by a row of bone screws. The nail is manipulated by a tool inserted through an aperture in the retaining plate. The nail is maintained at an adjusted distance from the bushing and plate by frictional engagement of a C-shaped retaining spring disposed between the outer wall of the nail and the inner wall of the bushing. Insertion and assembly of the C-shaped spring is accomplished through a pair of longitudinal slots in the outer wall of the nail which are angularly displaced relative to each other and a pin in the outer end of the bushing which passes between the free ends of the C-shaped spring.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which:

FIG. 1 is a front view in elevation of a fracture nail and retaining plate assembly, which is one emobidment of this invention implanted in a broken femur, which is shown in phantom outline;

FIG. 2 is an enlarged right end view in elevation of the assembly shown in FIG. 1;

FIG. 3 is a cross-sectional view taken through FIG. 2 along the line 3—3;

FIG. 4 is a cross-sectional view taken through FIG. 3 along the line 4—4;

FIG. 5 is a cross-sectional view taken through FIG. 3 along the line 5—5;

FIG. 6 is a cross-sectional view takne through FIG. 3 along the line 6—6;

FIG. 7 is a cross-sectional view taken through FIG. 3 along the line 7—7;

FIG. 7A is a cross-sectional view taken through FIG. 7 having a C-shaped spring removed;

FIG. 8 is a cross-sectional view takne through FIG. 3 along the line 8—8;

FIG. 9 is a cross-sectional view taken through FIG. 3 along the line 9—9;

FIG. 10 is a cross-sectional view taken through FIG. 3 along the line 10—10; and FIG. 11 is a cross-sectional view taken through FIG. 3 along the line 11—11.

DESCRIPTION OF THE PREFERRED EMBODIMENT

In FIG. 1 is shown a fracture nail and retaining plate assembly 10 made, for example, of biocompatible stainless steel, implanted in a femur 12 for securing its broken hip joint end 14 to the shaft 16. Insertion of the nail 18 into the broken ends of the femur is accomplished in the manner described in U.S. Pat. No. 2,937,642. Nail 18 is secured by three fins 20, which engage within hip joint portion 14 of femur 12.

Nail 18 is inserted in telescopic relationship within bushing 22 implanted in shaft 16 of femur 12. Nail 18 is implanted by use of a tool (not shown) which is engaged in threads 24 within the inner end 26 of nail 18 inserted within bushing 22, as shown in FIG. 3. The tool (not shown) passes through hole 28 in retaining plate 30, which is affixed to femur 12 by a row of bone screws (not shown) inserted through counter sunk screw holes 32 in retaining plate 30. Sliding engagement of slant end 34 of bushing 22 with retaining plate 30 is accomplished by engagement of triangular prongs 36 of plate 22 (shown in FIGS. 8-10) within corresponding grooves 38 in the wall of bushing 30 (shown in FIGS. 8 and 9). The ample cross sections of prongs 36 help make them rugged and durable. Their triangular configruation facilitates assembly, disassembly, adjustment and readjustment of the relative positions of bushing 22 and retaining plate 30.

The retention of nail 18 in its required telescopic position within bushing 22 is independently accomplished by C-shaped spring 40 (shwon in FIGS. 3 and 7) inserted between the outer wall of nail 18 and the inner wall of bushing 22. C-shaped spring 40 is placed around the shaft of nail 18 in a circumferential groove 42 connecting two longitudinal slots 44 and 46 on opposite sides of nail 18. These long slots 44 and 46 are shown in FIGS. 5, 6, 7 and 7A. The outside diameter of the C-shaped spring 40 in its relaxed state, is slightly larger than the inside diameter of the nail support bushing 22. The gap 48 in the C-shaped spring 40 is aligned with, and is slightly larger than the slot 46 on bottom of nail 18 as shown at FIG. 7. On assembly, nail 18 and spring 40 are rotated until the slot 46 and opening 48 in C-shaped spring 40 is in line with pin 52 in the end of bushing 22. Nail 18 is inserted into bushing 22 with pin 52 sliding in slot 46, until spring 40 is reached. Spring 40 is compressed to let it enter bushing 22, then nail 18 and spring 40 are pushed into bushing support member 22 until pin 52 comes up against the end of the longitudinal slot 46 and it rests in the opening 48 of the C-shaped spring 40. Nail 18 is then rotated 180° in circumferential groove 42 to bring pin 52 in line with the second longitudinal slot 44. Nail 18 can now be pushed as far in as needed. The pressure of spring 40 against the inside of bushing support member 22 holds nail 18 in place.

Fracture nail and retaining plate assembly 10 has the following advantages over previously available devices for the same purpose. The nail support bushing 22 and plate 30 (retaining element) are more heavily built, yielding a stronger device. Plate 30 has a bi-radius curvature 56 and 58 (FIG. 11) on its underside. This avoids cutting into the bone by sharp edges, but does not give excessive contact which would prevent circulation to and from the bone. Plate 30 has triangular cross section keys or prongs 36 holding nail support member, leading to easier assembly, disassembly, adjustment and readjustment. Nail support bushing 22 uses a C-shaped spring 40 to keep nail 18 in place, which is a very reliable holding means.

I claim:

1. A fracture nail plate assembly for connecting shaft and other portions of a broken bone together comprising an elongated nail having a splined end for implantation into a portion of the broken bone and a substantially smooth end for engagement in the assembly, a bushing for connecting the smooth end of the nail to the assembly, an elongated retaining plate, the bushing having a slanted end for engaging the retaining plate at an obtuse angle in accordance with the angle of engagement of the nail and retaining plate with different portions of the broken bone connected thereby, the retaining plate having convex outer and concave inner cross sections disposed perpendicularly to its length for engaging about the shaft of the bone, the retaining plate having inwardly directed flanges extending within its concave cross sections for connecting it to the slanted end of the bushing, the flanges having inwardly directed triangular cross sections and the outer surface of the slanted end of the bushing having corresponding grooves disposed parallel to its slanted end whereby the retaining plate is slidably engaged with the slanted end of the bushing for connecting them together, the retaining plate having a row of apertures for connecting it to the outside of the shaft of the bone, the smooth end of the nail being inserted within the bushing in telescopic relationship, a connection in the end of the smooth end of the nail to permit it to be manipulated by an elongated tool connected thereto, an aperture in the retaining plate in line with the connected bushing to permit access by the tool to the connection in the nail, a C-shaped spring having a gap disposed between the outer wall of the smooth end of the nail and inner portions of the bushing, a circumferential groove in a portion of the outer wall of the nail inserted within the bushing within which the C-shaped spring is engaged, a pair of longitudinal slots in the outer smooth wall of the nail on opposite sides of the circumferential groove, the slots being angularly displaced from each other to prevent a straight through passage through them and the gap in the C-shaped spring, a pin in the unconnected end of the C-shaped spring and extending therewithin, the pin being slightly narrower than the width of the slots whereby the nail and spring may be assembled into and rotatably locked within the bushing and the nail is angularly locked within the bushing.

2. A fracture nail plate assembly as set forth in claim 1, wherein the slots are angularly displaced 180° from each other.

3. A fracture nail plate assembly as set forth in claim 1, wherein the concave surface of the retaining plate has a shorter radius of curvature in the center and a slightly larger radius of curvature at its outsides to minimize the area of contact to the shaft of the bone.

* * * * *